US00PP36605P2

(12) United States Plant Patent
van Dijk

(10) Patent No.: US PP36,605 P2
(45) Date of Patent: Apr. 15, 2025

(54) ***ANTHURIUM* PLANT NAMED 'AN2973182'**

(50) Latin Name: *Anthurium andreanum*
Varietal Denomination: AN2973182

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/791,417

(22) Filed: Jul. 31, 2024

(51) Int. Cl.
*A01H 5/02* (2018.01)
*A01H 6/10* (2018.01)

(52) U.S. Cl.
USPC ..... Plt./369
CPC ..... *A01H 6/10* (2018.05)

(58) Field of Classification Search
USPC ..... Plt./369
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of cut flower *Anthurium* plant named 'AN2973182', characterized by its upright to outwardly arching plant habit; narrowly cordate dark green-colored leaves; large inflorescences that are positioned within to slightly above the foliar plane on strong and slightly outwardly scapes; inflorescences with two spathes; glossy and rugose red-colored spathes and lighter red-colored spadices; and durable spathes that impart good inflorescence longevity.

2 Drawing Sheets

Figure 1:
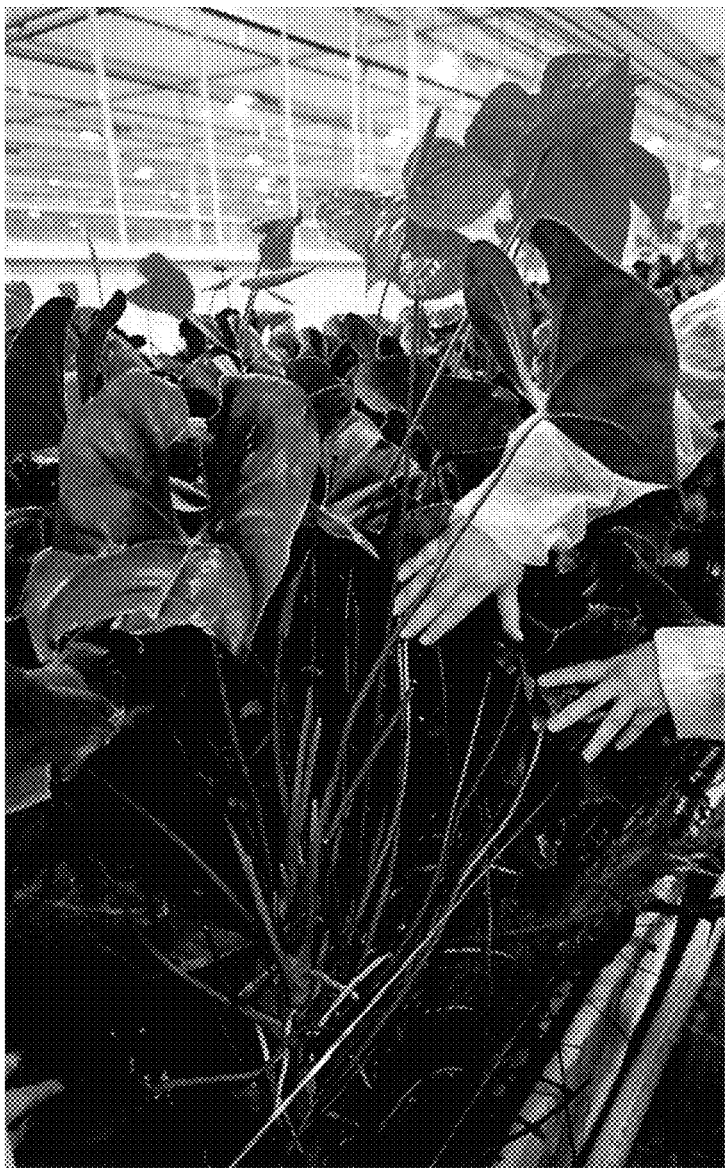

Botanical designation: *Anthurium andreanum.*
Cultivar denomination: 'AN2973182'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B. V. of Bleiswijk, The Netherlands on Nov. 22, 2023, application number 2023/2443. Foreign priority is not claimed to this application.

BACKGROUND OF THE INVENTION

The present invention relates to a new and distinct cultivar of *Anthurium* plant, botanically known as *Anthurium andreanum* and hereinafter referred to by the name 'AN2973182'.

The new *Anthurium* plant is a product of a controlled breeding program conducted by the Inventor in Bleiswijk, The Netherlands. The objective of the breeding program is to create new freely-clumping cut flower *Anthurium* plants with attractive red-colored, durable and glossy spathes.

The new *Anthurium* plant originated from a cross-pollination made by the Inventor in August 2001 in Bleiswijk, The Netherlands of a proprietary selection of *Anthurium andreanum* identified as code number 00-002340-0006, not patented, as the female, or seed, parent with a proprietary selection of *Anthurium andreanum* identified as code number 01-003366-0001, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in October 2004.

Asexual reproduction of the new *Anthurium* plant by in vitro meristem propagation in a controlled environment in Bleiswijk, The Netherlands since January 2009 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2973182'. These characteristics in combination distinguish 'AN2973182' as a new and distinct cut flower *Anthurium* plant:

1. Upright to outwardly arching plant habit.
2. Narrowly cordate dark green-colored leaves.
3. Large inflorescences that are positioned within to slightly above the foliar plane on strong and slightly outwardly scapes.
4. Inflorescences with two spathes.
5. Glossy and rugose red-colored spathes and lighter red-colored spadices.
6. Durable spathes that impart good inflorescence longevity.

Plants of the new *Anthurium* differ primarily from plants of the female parent selection in the following characteristics:

1. Spathes of plants of the new *Anthurium* are more rugose than spathes of plants of the female parent selection.

2. Spathes of plants of the new *Anthurium* are red in color whereas spathes of plants of the female parent selection are pink in color.

Plants of the new *Anthurium* differ primarily from plants of the male parent selection in the following characteristics:

1. Spathes of plants of the new *Anthurium* are not as large as spathes of plants of the male parent selection.
2. Spathes of plants of the new *Anthurium* are broadly cordate in shape whereas spathes of plants of the male parent selection are close to rotund in shape.

Plants of the new *Anthurium* can also be compared to plants of *Anthurium andreanum* 'Anthilci', not patented. In side-by-side comparisons, plants of the new *Anthurium* differ primarily from plants of 'Anthilci' in the following characteristics:

1. Spathes of plants of the new *Anthurium* are more rugose than spathes of plants of 'Anthilci'.
2. Spadices of plants of the new *Anthurium* are light red in color whereas spadices of plants of 'Anthilci' are green and white in color.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2973182' grown in a ground bed.

Figure 2:
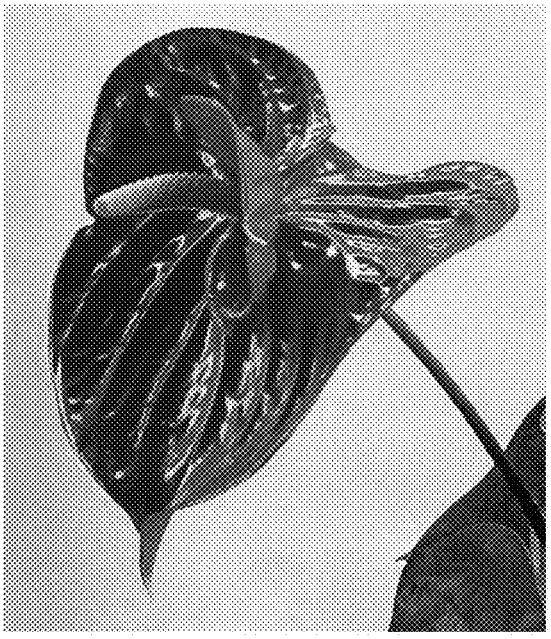
Figure 3:
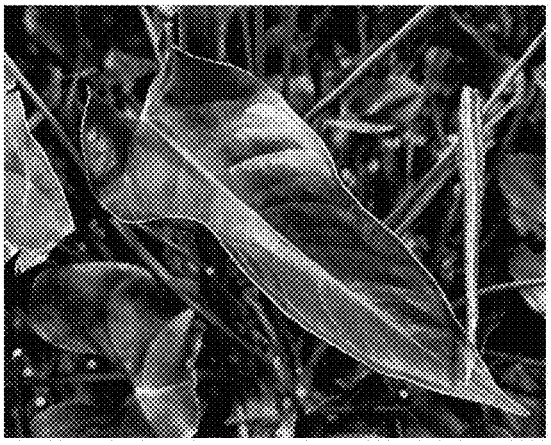

The photograph at the top of the second sheet (FIG. 2) is a close-up view of a typical inflorescence of 'AN2973182' and the photograph at the bottom of the second sheet (FIG. 3) is a close-up view of a typical leaf of 'AN2973182'.

DETAILED BOTANICAL DESCRIPTION

The aforementioned photographs and following observations and measurements describe plants grown in ground beds during the summer in a glass-covered greenhouse in Bleiswijk, The Netherlands. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were 6.5 years old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2973182'.

Parentage:

*Female, or seed, parent*.—Proprietary selection of *Anthurium andreanum* identified as code number 00-002340-0006, not patented.

*Male, or pollen, parent*.—Proprietary selection of *Anthurium andreanum* identified as code number 01-003366-0001, not patented.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically light yellowish white slightly tinged with pink in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly arching plant habit; overall shape, narrowly obovate.

*Growth habit*.—Non-clumping habit, grown as a cut flower with about six flowering stems developing per plant per year; moderately vigorous growth habit and moderate growth rate.

*Plant height, from soil level to top of leaf plane*.—About 139.7 cm.

*Plant height, from soil level to top of inflorescences*.—About 164.3 cm.

*Plant diameter or spread*.—About 71.3 cm.

Stem description:

*Length*.—About 93.5 cm.

*Diameter*.—About 2 cm.

*Internode length*.—About 3 cm.

*Aspect*.—Upright.

*Strength*.—Strong.

*Texture*.—Smooth, glabrous.

*Color, developing*.—Close to 143C.

*Color, developed*.—Close to 143A.

Leaf description:

*Arrangement*.—Alternate; simple; about eight leaves per stem.

*Length*.—About 39.1 cm.

*Width*.—About 19 cm.

*Shape*.—Narrowly cordate.

*Apex*.—Acuminate to apiculate with a mucronate tip.

*Base*.—Deeply cordate to auriculate; basal lobes free.

*Margin*.—Entire; moderately and coarsely undulate.

*Texture and luster, upper and lower surfaces*.—Smooth, glabrous; moderately leathery; glossy.

*Venation pattern*.—Pinnate.

*Color*.—Developing leaves, upper surface: Close to 200C and 200D; main vein, close to 144C. Developing leaves, lower surface: Close to 200D; main vein, close to N144D. Fully expanded leaves, upper surface: Close to a blend of 139A and 147A; venation, close to 143C. Fully expanded leaves, lower surface: Close to a blend of 146A and 146B; venation, close to 145A.

*Petioles*.—Length: About 50.8 cm. Diameter: Distally, about 4 mm; proximally, about 9 mm. Strength: Strong. Texture and luster, upper and lower surfaces: Smooth, glabrous; slightly glossy. Color, upper surface: Close to 144A. Color, lower surface: Close to a blend of 144A and 144B. Geniculum length: About 2.5 cm. Geniculum diameter: About 6 mm. Geniculum texture, upper and lower surfaces: Smooth, glabrous. Geniculum color, upper surface: Close to 144A. Geniculum color, lower surface: Close to a blend of 144A and 144B; towards the apex and base, close to a blend of 144B and 144C. Wing length:

About 6.1 cm. Wing diameter: About 3 mm. Wing color: Close to 144A; towards the margins, close to 144B to 144C.

Inflorescence description:

*Inflorescence arrangement and flowering habit.*—Spathes with spadices held within and slightly above the foliar plane on strong and erect scapes; inflorescences with a main spathe and a smaller secondary spathe; inflorescences arising from leaf axils; freely and continuous flowering year-round in controlled temperature greenhouses in The Netherlands; typically about three developing and developed inflorescences per plant at one time; inflorescence development commences about 18 months after planting.

*Inflorescence longevity.*—Depending on temperature, spathes maintain good substance for about five weeks as a cut flower; inflorescences persistent.

*Fragrance.*—None detected.

*Spathes.*—Length, main spathe: About 19.3 cm. Width, main spathe: About 14.2 cm. Length, secondary spathe: About 8.6 cm. Width, secondary spathe: About 8.2 cm. Shape, main spathe: Broadly and slightly elongated cordate; typically flat to slightly concave or slightly convex. Shape, secondary spathe: Broadly cordate to cordate; strongly concave to slightly convex. Apex, main spathe: Apiculate with a mucronate tip. Apex, secondary spathe: Abruptly acute to apiculate with a mucronate tip. Base, main spathe: Deeply cordate to auriculate. Base, secondary spathe: Cordate to deeply truncate. Margin, main and secondary spathes: Entire; slightly and coarsely undulate. Aspect, main spathe: About 100° from the scape axis. Aspect, secondary spathe: About 75° from the scape axis and about 30° to 115° from main spathe axis. Texture and luster, main and secondary spathes, upper and lower surfaces: Smooth, glabrous; moderately leathery; strongly rugose; glossy. Color, main spathe: When developing, front surface: Close to N45B; at the apex, close to N144B. When developing, rear surface: Close to a blend of 45A and 45B; at the apex, close to N144B. Fully developed, front surface: Close to a blend of 45B and N45B; at the apex, close to 145C; color does not change with subsequent development. Fully developed, rear surface: Close to N45B; at the apex, close to 145C; color does not change with subsequent development. Color, secondary spathe: When developing, front surface: Close to 45A and 45B. When developing, rear surface: Close to 50A and 50B; towards the apex, close to 45C and at the apex, close to 145C. Fully developed, front surface: Close to 45B; at the apex, close to 145C to 145D; color does not change with subsequent development. Fully developed, rear surface: Close to a blend of 45C and 50A; at the apex, close to 145C to 145D; color does not change with subsequent development.

*Spadices.*—Length: About 7.1 cm. Diameter: Proximally, about 1.2 cm and distally, about 8 mm. Shape: Columnar, slightly tapering towards the apex; apex, obtuse; base, obtuse; in cross-section, rounded. Aspect: About 30° to 50° from the scape axis and about 22.5° from the main spathe axis. Color: Immature: Close to 31A; distally, close to 31B. Mature: Close to a blend of 54B and 58D; distally, close to 52A. Flowers: Type: Hermaphroditic. Quantity per spadix: Numerous, about 500.Height: About 0.1 mm. Diameter: About 2.5 mm. Shape: Roughly square. Anther color: Close to a blend of 54B and 58D. Pollen amount: Moderate. Pollen color: Close to 155B. Stigma color: Close to 76C.

*Scapes.*—Length: About 76.2 cm. Diameter: About 5.5 mm. Strength: Strong. Aspect: About 30° from vertical. Color: Close to 152A; distally, close to N144A; towards the base, close to 144B; if exposed to sunlight, distally, variably tinged with close to N199B and 200D.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2973182' as herein illustrated and described.

* * * * *